United States Patent
Asirvatham et al.

(10) Patent No.: US 11,795,143 B2
(45) Date of Patent: Oct. 24, 2023

(54) AMINO ACID SURFACTANTS

(71) Applicant: AdvanSix Resins & Chemicals LLC, Parsippany, NJ (US)

(72) Inventors: Edward Asirvatham, Chatham, NJ (US); Andrei Honciuc, Iasi (RO); Voichita Mihali, Basel (CH)

(73) Assignee: AdvanSix Resins & Chemicals LLC, Parsippany, NJ (US)

( * ) Notice: Subject to any disclaimer, the term of this patent is extended or adjusted under 35 U.S.C. 154(b) by 142 days.

(21) Appl. No.: 17/154,916

(22) Filed: Jan. 21, 2021

(65) Prior Publication Data

US 2021/0230108 A1   Jul. 29, 2021

Related U.S. Application Data

(60) Provisional application No. 62/967,177, filed on Jan. 29, 2020.

(51) Int. Cl.
*C11D 1/12*  (2006.01)
*C11D 1/75*  (2006.01)
(Continued)

(52) U.S. Cl.
CPC ............ *C07C 309/14* (2013.01); *A61K 8/466* (2013.01); *A61Q 5/02* (2013.01); *A61Q 5/12* (2013.01);
(Continued)

(58) Field of Classification Search
CPC .. C11D 1/12; C11D 1/665; C11D 1/75; C11D 3/26; C11D 3/34; C11D 7/32;
(Continued)

(56) References Cited

U.S. PATENT DOCUMENTS

| 3,213,500 A | 10/1965 | Thompson |
| 3,704,486 A | 12/1972 | Blacklock |

(Continued)

FOREIGN PATENT DOCUMENTS

| CA | 2006439 A1 | 7/1990 |
| CN | 105802600 A | 7/2016 |

(Continued)

OTHER PUBLICATIONS

Research Disclosure, "Detergent compositions and fabric conditioning compositions containing dye transfer inhibiting polymers." No. 411, Jul. 1998, pp. 935-953.

(Continued)

*Primary Examiner* — Brian P Mruk
(74) *Attorney, Agent, or Firm* — Faegre Drinker Biddle & Reath LLP

(57) ABSTRACT

The present disclosure provides derivatives of amino acids that have surface-active properties. The amino acid can be naturally-occurring or synthetic, or they may be obtained via a ring-opening reaction of a lactam, such as caprolactam. The amino acid may be functionalized to form a compound that is surface-active and have advantageous surfactant characteristics. The compounds of the present disclosure have low critical micelle concentrations (CMC) as well as superior ability to lower the surface tension of a liquid.

6 Claims, 2 Drawing Sheets

(51) Int. Cl.

| | | |
|---|---|---|
| C11D 3/26 | (2006.01) | |
| C11D 3/34 | (2006.01) | |
| C11D 7/32 | (2006.01) | |
| C11D 7/34 | (2006.01) | |
| C11D 11/00 | (2006.01) | |
| A61K 8/46 | (2006.01) | |
| C07C 303/22 | (2006.01) | |
| C07C 309/14 | (2006.01) | |
| A61Q 5/02 | (2006.01) | |
| A61Q 5/12 | (2006.01) | |
| C11D 1/26 | (2006.01) | |
| C09K 23/00 | (2022.01) | |

(52) U.S. Cl.
CPC ............ *C07C 303/22* (2013.01); *C09K 23/00* (2022.01); *C11D 1/26* (2013.01)

(58) Field of Classification Search
CPC .. C11D 7/34; C11D 11/00; A61K 8/46; C07C 303/22; C07C 309/14
See application file for complete search history.

(56) References Cited

U.S. PATENT DOCUMENTS

| | | | |
|---|---|---|---|
| 4,276,460 A | 6/1981 | Haesly et al. | |
| 4,297,769 A | 11/1981 | Coules | |
| 4,432,881 A | 2/1984 | Evani | |
| 4,502,193 A | 3/1985 | Harmon et al. | |
| 4,664,458 A | 5/1987 | Worth | |
| 5,060,100 A | 10/1991 | Mihara et al. | |
| 5,580,203 A | 12/1996 | Read et al. | |
| 5,706,559 A | 1/1998 | Oliver et al. | |
| 5,798,095 A | 8/1998 | Racky | |
| 5,958,894 A | 9/1999 | Heath et al. | |
| 5,972,323 A | 10/1999 | Lang et al. | |
| 6,114,757 A | 9/2000 | Delprete | |
| 6,304,986 B1 | 10/2001 | Ma et al. | |
| 6,501,030 B1 | 12/2002 | Parizi et al. | |
| 6,702,592 B1 | 3/2004 | Harden et al. | |
| 7,646,556 B1 | 1/2010 | Kose et al. | |
| 7,653,847 B1 | 1/2010 | Liikanen et al. | |
| 7,768,736 B2 | 8/2010 | Belmont et al. | |
| 8,599,507 B2 | 12/2013 | Sanvido et al. | |
| 8,964,320 B1 | 2/2015 | Hu et al. | |
| 9,142,246 B1 | 9/2015 | Trantham et al. | |
| 9,484,059 B2 | 11/2016 | Lim et al. | |
| 9,552,846 B1 | 1/2017 | Lim | |
| 9,580,535 B2 | 2/2017 | Wilson et al. | |
| 2003/0081357 A1 | 5/2003 | Hong et al. | |
| 2008/0259100 A1 | 10/2008 | Rengaswamy et al. | |
| 2017/0079898 A1* | 3/2017 | Fevola ..................... | C11D 1/00 |
| 2017/0081277 A1* | 3/2017 | Boaz ..................... | C09K 23/018 |
| 2018/0117157 A1 | 5/2018 | Soula et al. | |
| 2020/0370404 A1 | 11/2020 | Gizzatov et al. | |
| 2021/0229053 A1 | 7/2021 | Berlia et al. | |
| 2021/0230100 A1 | 7/2021 | Asirvatham et al. | |
| 2021/0230106 A1 | 7/2021 | Asirvatham et al. | |
| 2021/0230107 A1 | 7/2021 | Asirvatham et al. | |
| 2021/0283030 A1 | 9/2021 | Asirvatham | |
| 2021/0284896 A1 | 9/2021 | Asirvatham | |
| 2021/0284936 A1 | 9/2021 | Asirvatham | |
| 2021/0289776 A1 | 9/2021 | Asirvatham | |
| 2021/0290765 A1 | 9/2021 | Asirvatham | |
| 2021/0292583 A1 | 9/2021 | Asirvatham | |
| 2021/0292647 A1 | 9/2021 | Asirvatham | |

FOREIGN PATENT DOCUMENTS

| | | |
|---|---|---|
| CN | 106750342 A | 5/2017 |
| CN | 108024935 A | 5/2018 |
| DE | 3939746 A1 | 6/1991 |
| DE | 29622184 U1 | 2/1997 |
| DE | 10021538 A1 | 12/2001 |
| EP | 0385562 A2 | 9/1990 |
| EP | 0638236 A1 | 2/1995 |
| EP | 0826661 A2 | 3/1998 |
| EP | 1000544 A1 | 5/2000 |
| GB | 2204740 A | 11/1988 |
| GB | 2310659 A | 9/1997 |
| GB | 2311033 A | 9/1997 |
| JP | 61-278341 A | 12/1986 |
| JP | 01-190798 A | 7/1989 |
| JP | 04-349284 A | 12/1992 |
| JP | 08-007556 A | 1/1996 |
| JP | 09-266021 A | 10/1997 |
| JP | 11-233910 A | 8/1999 |
| JP | 2006-294170 A | 10/2006 |
| JP | 4156467 B2 | 9/2008 |
| JP | 2017-195029 A | 10/2017 |
| TW | 200904971 A | 2/2009 |
| WO | 97/31889 A1 | 9/1997 |
| WO | 98/45233 A2 | 10/1998 |
| WO | 03/68377 A1 | 8/2003 |
| WO | 2012/061093 A1 | 5/2012 |
| WO | 2017/012087 A1 | 1/2017 |
| WO | 2017/048555 A1 | 3/2017 |
| WO | 2017/199921 A1 | 11/2017 |
| WO | 2018/115191 A1 | 6/2018 |

OTHER PUBLICATIONS

International Search Report and Written Opinion received for PCT Patent Application No. PCT/US2021/014440, dated Apr. 30, 2021, 9 pages.

International Search Report and Written Opinion received for PCT Patent Application No. PCT/US2021/014444, dated Apr. 26, 2021, 12 pages.

International Search Report and Written Opinion received for PCT Patent Application No. PCT/US2021/014445, dated Apr. 26, 2021, 9 pages.

International Search Report and Written Opinion received for PCT Patent Application No. PCT/US2021/014447, dated Apr. 30, 2021, 9 pages.

International Search Report and Written Opinion received for PCT Patent Application No. PCT/US2021/014457, dated Apr. 30, 2021, 8 pages.

Novotny, M., et al., "Transkarbams as transdermal permeation enhancers: effects of ester position and ammonium carbamate formation," Bioorganic & medicinal chemistry letters, vol. 20, No. 9, May 1, 2010, pp. 2726-2728.

Yasa, S.R., et al., "Synthesis, characterization, antimicrobial and biofilm inhibitory activities of new N-oxide esters," Medicinal Chemistry Research, vol. 26, No. 8, Apr. 3, 2017, pp. 1689-1696.

Hrabálek et al., "Esters of omega-amino acids as flexible penetration enhancers", Pharmazie, vol. 49, No. 5, May 1994, pp. 325-328.

International Search Report and Written Opinion received for PCT Patent Application No. PCT/US2021/021565, dated Jun. 18, 2021, 13 pages.

International Search Report and Written Opinion received for PCT Patent Application No. PCT/US2021/021569, dated May 17, 2021, 9 pages.

International Search Report and Written Opinion received for PCT Patent Application No. PCT/US21/21571, dated Jul. 9, 2021, 9 pages.

International Search Report and Written Opinion received for PCT Patent Application No. PCT/US21/21574, dated Jul. 1, 2021, 10 pages.

International Search Report and Written Opinion received for PCT Patent Application No. PCT/US21/21595, dated Jul. 30, 2021, 15 pages.

International Search Report and Written Opinion received for PCT Patent Application No. PCT/US21/21596, dated Jun. 22, 2021, 10 pages.

International Search Report and Written Opinion received for PCT Patent Application No. PCT/US21/21597, dated Aug. 9, 2021, 11 pages.

(56) References Cited

OTHER PUBLICATIONS

Kerry P. Mahon et al: "Combinatorial Approach to Determine Functional Group Effects on Lipidoid-Mediated si RNA Delivery", Bioconjugate Chemistry, vol. 21, No. 8, Aug. 18, 2010 (Aug. 18, 2010), pp. 1448-1454.
Invitation to Pay Additional Fees received for PCT Patent Application No. PCT/US21/21595, dated Jun. 9, 2021, 9 pages.
Invitation to Pay Additional Fees received for PCT Patent Application No. PCT/US21/21597, dated Jun. 17, 2021, 7 pages.

* cited by examiner

AMINO ACID SURFACTANTS

CROSS-REFERENCE TO RELATED APPLICATION

This application claims priority to U.S. Provisional Application No. 62/967,177, filed Jan. 29, 2020, the disclosure of which is herein incorporated by reference in its entirety.

FIELD

The present disclosure pertains to derivatives of amino acids and methods for their synthesis, wherein the amino acid derivatives have surface-active properties.

BACKGROUND

Surfactants (molecules with surface-active properties) are an important class of molecules with highly sought-after characteristics. Surfactants may be uncharged, zwitterionic, cationic, or anionic. Often, these compounds are amphiphilic molecules with a water-insoluble hydrophobic "tail" group and a water-soluble hydrophilic "head" group. These compounds may adsorb at an interface, such as an interface between two liquids, a liquid and a gas, or a liquid and a solid. In the case of an interface between water and oil, the hydrophilic head group extends into the water, while the hydrophobic tail extends into the oil. When added to water, the hydrophilic head group extends into the water, while the hydrophobic tail extends into the air. The presence of the surfactant disrupts the intermolecular interaction between water molecules, replacing it with weaker interactions between water molecules and the surfactant. This results in lowered surface tension and can also serve to stabilize the interface.

At sufficiently high concentrations, surfactants may form aggregates to limit the exposure of the hydrophobic tail to the polar solvent. One such aggregate is a micelle, in which the molecules are arranged in a sphere with the hydrophobic tails inside the sphere and the hydrophilic heads on the outside to interact with a polar solvent. The effect that a given compound has on surface tension and the concentration at which it forms micelles may serve as defining characteristics for a surfactant.

Surfactants are widely used in commercial applications in formulations ranging from detergents to hair care products to cosmetics. Compounds with surface-active properties are used as soaps, detergents, lubricants, wetting agents, foaming agents, and spreading agents, among others. Thus, there is an ongoing need to identify and synthesize such compounds.

However, solely from its structure, it may be difficult to predict whether a given compound would have surface-active properties, let alone other important characteristics such as interfacial adsorption dynamics, minimum surface tension achievable, and/or ability to wet hydrophobic and/or oleophobic surfaces, which are also integral to whether the compound would become a useful surfactant. Certain amino acids and their derivatives, for example, are desirable as building blocks for surfactants, but the selection of which amino acids to use is far from intuitive. Synthesis of such compounds adds another layer of difficulty due to the differences of solubilities attributable to different elements and moieties present in the same molecules. There remains a need for high-efficacy surfactants that can be readily synthesized at commercial scale via straightforward routes.

SUMMARY

The present disclosure provides derivatives of amino acids that have surface-active properties. The amino acids may be naturally occurring or synthetic amino acids, or they may be obtained via ring-opening reactions of molecules such as lactams, for example caprolactam. The amino acids may be functionalized to form compounds with surface-active properties. Characteristically, these compounds may have low critical micelle concentrations (CMC) and/or the ability to reduce the surface tension of a liquid.

The present disclosure provides compounds of Formula I, below, also referred to herein as the surfactant:

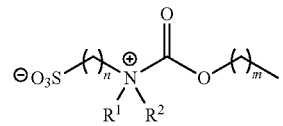

Formula I wherein $R^1$ and $R^2$ are independently chosen from $C_1$-$C_6$ alkyl, namely $C_1$, $C_2$, $C_3$, $C_4$, $C_5$, or $C_6$; n is an integer from 2 to 5, namely 2, 3, 4, or 5; and m is an integer from 9 to 20, namely 9, 10, 11, 12, 13, 14, 15, 16, 17, 18, 19, or 20. The present disclosure in particular provides compounds of Formula II, below, also referred to herein as the surfactant:

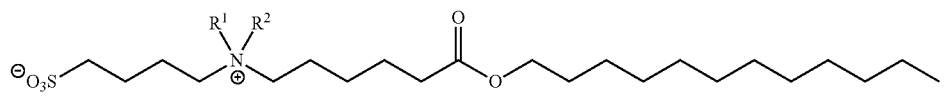

Formula II wherein $R^1$ and $R^2$ are independently chosen from $C_1$-$C_6$ alkyl, namely $C_1$, $C_2$, $C_3$, $C_4$, $C_5$, or $C_6$.

One specific compound provided by the present disclosure is 4-((6-(dodecyloxy)-6-oxohexyl)dimethylammonio)butane-1-sulfonate, having the following formula:

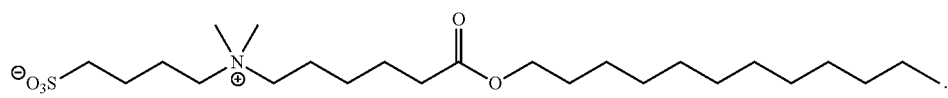

The above mentioned and other features of the disclosure, and the manner of attaining them, will become more apparent and will be better understood by reference to the following description of embodiments taken in conjunction with the accompanying drawings.

DETAILED DESCRIPTION

Figure 1:
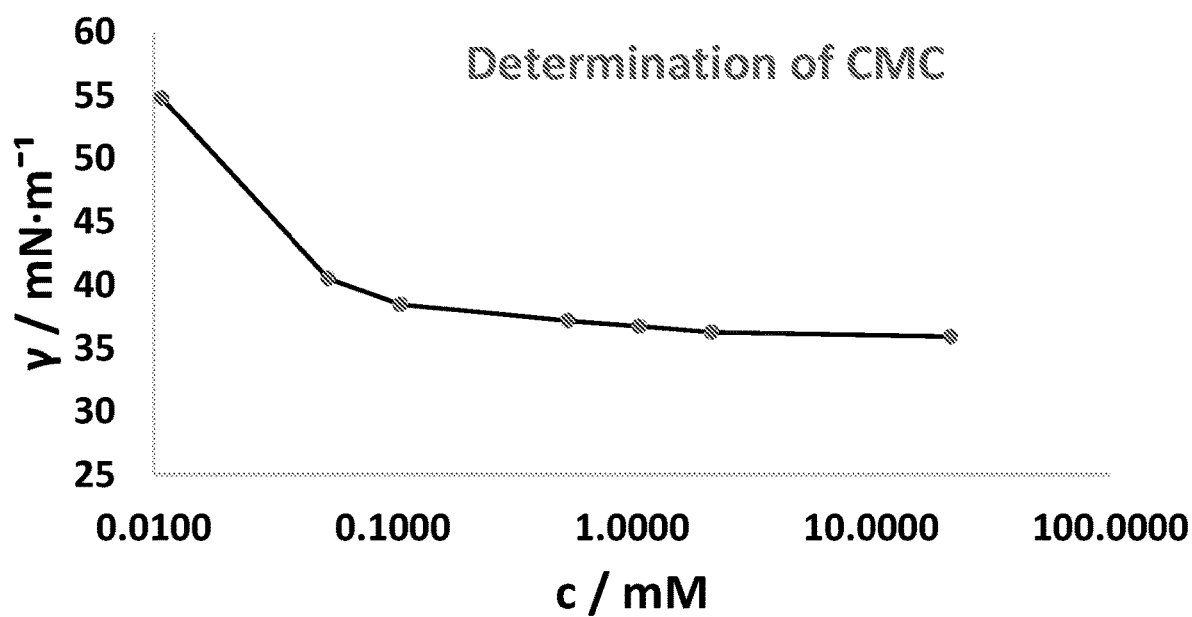
FIG. 1 shows a plot of surface tension versus concentration measured at pH=7 as described in Example 2, wherein the Y axis depicts the surface tension (γ) in millinewtons per meter (mN/m) and the X axis depicts the concentration (c) in millimoles (mM).

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

As used herein, the word "alkyl" means any saturated carbon chain, which may be a straight or branched chain.

As used herein, the phrase "surface-active" means that the associated compound is able to lower the surface tension of the medium in which it is dissolved, and/or the interfacial tension with other phases, and, accordingly, may be adsorbed at the liquid/vapor and/or other interfaces. The term "surfactant" may be applied to such a compound.

With respect terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error or minor adjustments made to optimize performance, for example. In the event it is determined that individuals having ordinary skill in the relevant arts would not readily ascertain values for such reasonably small differences, the terms "about" and "approximately" can be understood to mean plus or minus 10% of the stated value.

The present disclosure provides derivatives of amino acids. The amino acids may be naturally occurring or synthetic, or they may be obtained from ring-opening reactions of lactams, such as caprolactam. The compounds of the present disclosure have been shown to have surface-active properties, and may be used as surfactants and wetting agents, for example. In particular, the present disclosure provides compounds of Formula I, shown below:

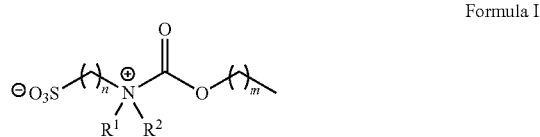

Formula I wherein $R^1$ and $R^2$ are independently chosen from $C_1$-$C_6$ alkyl, namely $C_1$, $C_2$, $C_3$, $C_4$, $C_5$, or $C_6$; n is an integer from 2 to 5, namely 2, 3, 4, or 5; and m is an integer from 9 to 20, namely 9, 10, 11, 12, 13, 14, 15, 16, 17, 18, 19, or 20.

Alternatively, the present disclosure also provides for compounds of Formula II, shown below:

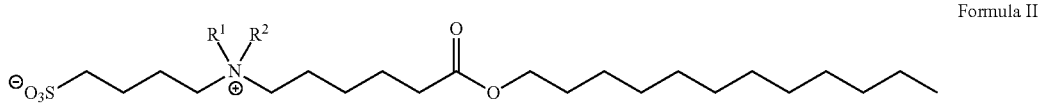

Formula II wherein $R^1$ and $R^2$ are independently chosen from $C_1$-$C_6$ alkyl, namely $C_1$, $C_2$, $C_3$, $C_4$, $C_5$, or $C_6$.

One specific compound provided by the present disclosure is 4-((6-(dodecyloxy)-6-oxohexyl)dimethylammonio)butane-1-sulfonate, having the following formula:

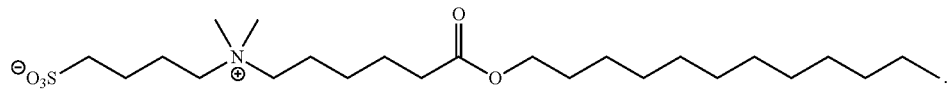

These compounds may be synthesized by various methods. One such method includes opening a lactam to yield an amino acid having an N-terminus and reacting the N-terminus of the amino acid with an alkylating agent to yield a tertiary amine. The resulting tertiary amine may then react with an alcohol under acidic conditions to provide an amino acid ester having an N-terminus. The amino acid ester N-terminus may then react with sulfonating agent to yield the desired sulfonate.

The amino acid may be naturally occurring or synthetic or may be derived from a ring opening reaction of a lactam, such as propiolactam, butyrolactam, valerolactam, and caprolactam, for example. The ring-opening reaction may be either an acid or alkali catalyzed reaction, and an example of an acid catalyzed reaction is shown below in Scheme 1.

SCHEME 1

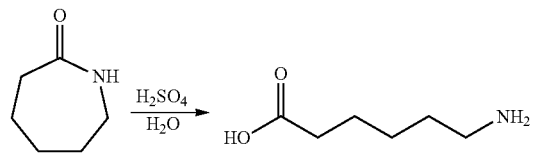

The amino acid may have as few as 2 or as many as 5, namely 2, 3, 4, or 5, carbons between the N- and C-terminii.

The alkyl chain may be branched or straight. The alkyl chain may be interrupted with nitrogen, oxygen, or sulfur. The alkyl chain may be further substituted with one or more substituents selected from the group consisting of hydroxyl, amino, amido, sulfonyl, sulfonate, carboxyl, and carboxylate. The N-terminal nitrogen may be acylated or alkylated with one or more alkyl groups. For example, the amino acid may be 6-(dimethylamino)hexanoic acid.

The derivative of the amino acid may be synthesized as shown below in Scheme 2. As shown, 6-aminohexanoic acid is treated with formaldehyde in formic acid at reflux to give 6-(dimethylamino)hexanoic acid. The free carboxylic acid is then treated with an alcohol, such as dodecanol, in the presence of p-toluene sulfonic acid (PTSA) in toluene to give the corresponding ester, dodecyl 6-(dimethylamino) hexanoate. The N-terminus is then treated with 1,4-butanesultone in refluxing ethyl acetate to yield the desired sulfonate.

wherein l is equal to the wetted perimeter (2w+2d, in which w and d are the plate thickness and width, respectively) and cos θ, the contact angle between the liquid and the plate, is assumed to be 0 in the absence of an extant literature value.

Another parameter used to assess the performance of surfactants is dynamic surface tension. The dynamic surface tension is the value of the surface tension for a particular surface or interface age. In the case of liquids with added surfactants, this can differ from the equilibrium value. Immediately after a surface is produced, the surface tension is equal to that of the pure liquid. As described above, surfactants reduce surface tension; therefore, the surface tension drops until an equilibrium value is reached. The time required for equilibrium to be reached depends on the diffusion rate and the adsorption rate of the surfactant.

One method by which dynamic surface tension is measured relies upon a bubble pressure tensiometer. This device measures the maximum internal pressure of a gas bubble

SCHEME 2

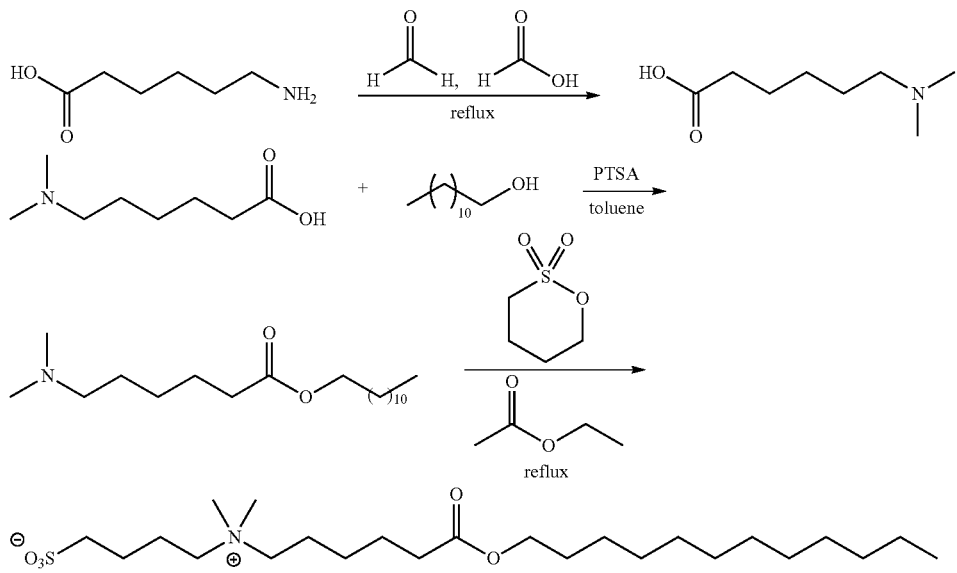

The compounds of the present disclosure demonstrate surface-active properties. These properties may be measured and described by various methods. One method by which surfactants may be described is by the molecule's critical micelle concentration (CMC). CMC may be defined as the concentration of a surfactant at which micelles form, and above which all additional surfactant is incorporated into micelles.

As surfactant concentration increases, surface tension decreases. Once the surface is completely overlaid with surfactant molecules, micelles begin to form. This point represents the CMC, as well as the minimum surface tension. Further addition of surfactant will not further affect the surface tension. CMC may therefore be measured by observing the change in surface tension as a function of surfactant concentration. One such method for measuring this value is the Wilhemy plate method. A Wilhelmy plate is usually a thin iridium-platinum plate attached to a balance by a wire and placed perpendicularly to the air-liquid interface. The balance is used to measure the force exerted on the plate by wetting. This value is then used to calculate the surface tension (γ) according to Equation 1:

$\gamma = F/l \cos \theta$    Equation 1:

that is formed in a liquid by means of a capillary. The measured value corresponds to the surface tension at a certain surface age, the time from the start of the bubble formation to the occurrence of the pressure maximum. The dependence of surface tension on surface age can be measured by varying the speed at which bubbles are produced.

Surface-active compounds may also be assessed by their wetting ability on solid substrates as measured by the contact angle. When a liquid droplet comes in contact with a solid surface in a third medium, such as air, a three-phase line forms among the liquid, the gas and the solid. The angle between the surface tension unit vector, acting at the three-phase line and tangent at the liquid droplet, and the surface is described as the contact angle. The contact angle (also known as wetting angle) is a measure of the wettability of a solid by a liquid. In the case of complete wetting, the liquid is completely spread over the solid and the contact angle is 0°. Wetting properties are typically measured for a given compound at the concentration of 1-100×CMC, however, it is not a property that is concentration-dependent therefore measurements of wetting properties can be measured at concentrations that are higher or lower.

In one method, an optical contact angle goniometer may be used to measure the contact angle. This device uses a digital camera and software to extract the contact angle by analyzing the contour shape of a sessile droplet of liquid on a surface.

Potential applications for the surface-active compounds of the present disclosure include formulations for use as shampoos, hair conditioners, detergents, spot-free rinsing solutions, floor and carpet cleaners, cleaning agents for graffiti removal, wetting agents for crop protection, adjuvants for crop protection, and wetting agents for aerosol spray coatings.

It will be understood by one skilled in the art that small differences between compounds may lead to substantially different surfactant properties, such that different compounds may be used with different substrates, in different applications.

The following non-limiting embodiments are provided to demonstrate the different properties of the different surfactants.

The compounds are effective as surface-active agents, useful for wetting or foaming agents, dispersants, emulsifiers, and detergents, among other applications.

The compounds of the present disclosure may be useful in both the applications described above and some further special applications such as surface treatments, such as in personal hair care products, and can also be used to generate water repellant surfaces.

The amount of the compounds disclosed herein used in a formulation may be as low as about 0.001 wt. %, about 0.05 wt. %, about 0.1 wt. %, about 0.5 wt. %, about 1 wt. %, about 2 wt. %, or about 5 wt. %, or as high as about 8 wt. %, about 10 wt. %, about 15 wt. %, about 20 wt. %, or about 25 wt. %, or within any range defined between any two of the foregoing values.

EXAMPLES

Nuclear magnetic resonance (NMR) spectroscopy was performed on a Bruker 500 MHz spectrometer. The critical micelle concentration (CMC) was determined by the Wilhelmy plate method at 23° C. with a tensiometer (DCAT 11, DataPhysics Instruments GmbH) equipped with a Pt—Ir plate. Dynamic surface tension was determined with a bubble pressure tensiometer (Krüss BP100, Krüss GmbH), at 23° C. Contact angle was determined with the optical contact angle goniometer (OCA 15 Pro, DataPhysics GmbH) equipped with a digital camera.

Example 1

Synthesis of 4-((6-(dodecyloxy)-6-oxohexyl)dimethylammonio)butane-1-sulfonate 6-(Dimethylamino)hexanoic acid (11.99 g, 75.36 mmol) was dissolved in toluene (50 mL) in a round bottom flask equipped with a Dean-Stark trap. Dodecanol (12.68 g, 75.36 mmol) and p-toluene sulfonic acid monohydrate (PTSA) (14.33 g, 75.36 mmol) were then added. The reaction was heated to reflux for 24 hours, until no further water was noted in the Dean-Stark trap. The solvent was removed under vacuum and the resultant solid was washed with hexanes. The solid was dissolved in dichloromethane (200 mL) and washed with saturated sodium carbonate to give dodecyl 6-(dimethylamino)hexanoate in 51% yield. $^1$H NMR (DMSO) δ 4.00 (t, J=6.5 Hz, 2H), 2.27 (t, J=7.3 Hz, 2H), 2.13-2.16 (m, 2H), 2.01 (s, 6H), 1.54-1.53 (m, 6H), 1.27-1.18 (m, 20H), 0.86 (t, 3H).

Dodecyl 6-(dimethylamino)hexanoate (1.0 g, 3.05 mmol) was dissolved in ethyl acetate (30 mL). 1,4-Butanesultone (0.62 g, 4.57 mmol) was then added, and the mixture was heated to reflux for 12 hours. The reaction was cooled to room temperature, and the solvent was removed under vacuum. $^1$H NMR (DMSO) δ 4.00 (t, J=6.7 Hz, 2H), 3.29-3.15 (m, 4H), 2.97 (s, 6H), 2.47 (t, J=7.4 Hz, 2H), 2.33 (t, J=7.4 Hz, 2H), 1.81-1.70 (m, 2H), 1.66-1.55 (m, 6H), 1.32-1.23 (m, 20H), 0.86 (t, J=6.9 Hz, 3H).

Example 2

Determination of Critical Micelle Concentration (CMC)

The critical micelle concentration (CMC) was tested. From the change in surface tension with concentration in water, the CMC was determined to be about 0.1 mmol. The plateau value of minimum surface tension that can be reached by this surfactant is about 38 mN/m, namely 38 mN/m±3.8 mN/m. FIG. 1 is a plot of these results, showing surface tension versus concentration. From the plot of the results, the surface tension at the CMC is about 38 mN/m, and the surface tension is equal to or less than 37 mN/m at a concentration of 1 mmol or greater.

Example 3

Determination of Dynamic Surface Tension

Figure 2:
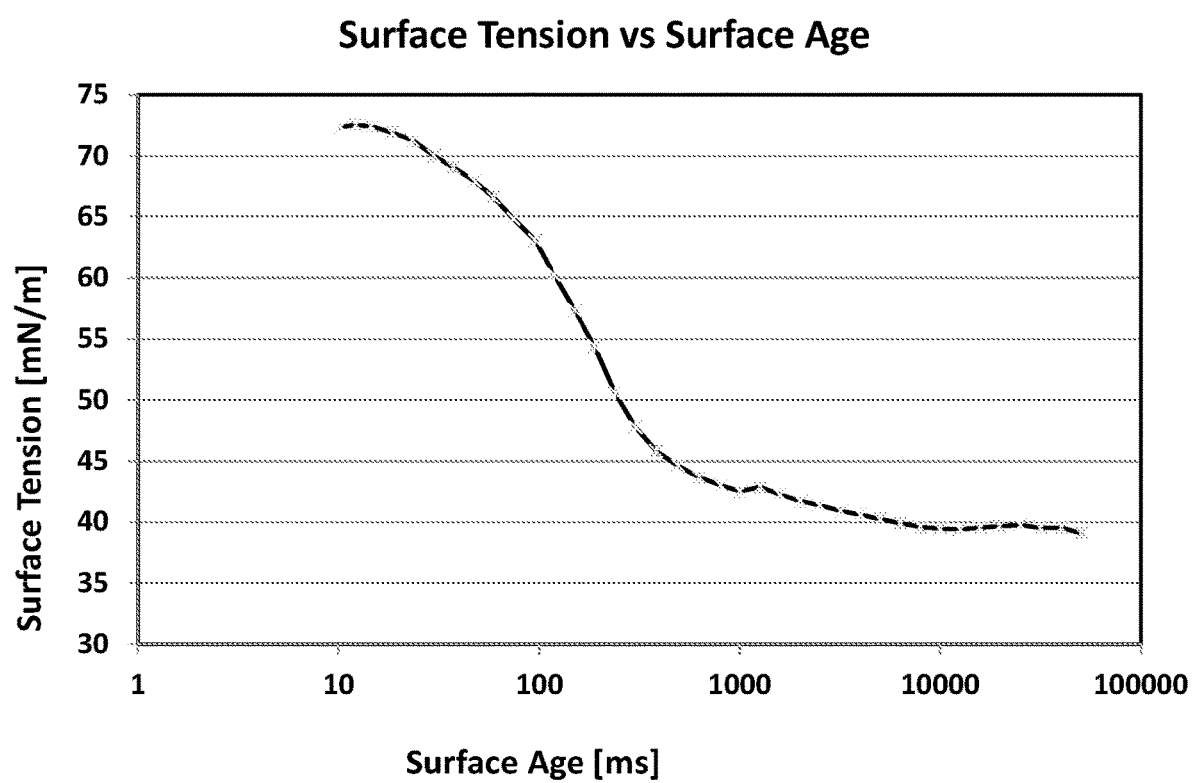
FIG. 2 shows a plot of dynamic surface tension as change in surface tension versus time as described in Example 3, wherein the Y axis depicts the surface tension in millinewtons per meter (mN/m) and the X axis depicts the surface age in milliseconds (ms).

The dynamic surface tension was determined with a bubble pressure tensiometer which measures the change of surface tension of a freshly created air-water interface with time. FIG. 2 presents a plot of the surface tension versus time, showing that the compound fully saturated the surface in approximately 1 second. From the plot, the dynamic surface tension is equal to or less than 40.5 mN/m at a surface age of 4000 ms or greater.

Example 4

Determination of Wetting Properties

In addition to surface tension and surface dynamics, the wetting properties of the compound were tested on various surfaces. For example, hydrophobic substrates such as polyethylene-HD exhibit surface wetting with a contact angle of 46.5°. On oleophobic and hydrophobic substrates such as Teflon, the measured contact angle was much less than that of water, 62.7° (Table 1).

TABLE 1

| Substrate | CA of Surfactant (°) | Concentration | CA of water (°) |
|---|---|---|---|
| Teflon | 62.7 | 10× CMC | 119 |
| Polyethylene-HD | 46.5 | 10× CMC | 93.6 |
| Nylon | 25.7 | 10× CMC | 50 |
| Polyethylene terephthalate | 35.6 | 10× CMC | 65.3 |
| | | 10× CMC | |

Example 5

Formulation for Shampoo

In this Example, a formulation for use as a shampoo is provided. This formulation is useful in in providing hair with a smooth and silky feel. The components of the formulation are shown below in Table 2. Additionally, the formulation may include other natural oils and ingredients, as well as vitamins for consumer appeal, in an amount of less than 1 wt. %.

TABLE 2

| Component | Function | Weight % |
| --- | --- | --- |
| Surfactant | Surfactant | 0.1-10 |
| Ammonium lauryl sulfate | Foaming agent | 10-25 |
| Cocamidopropyl betaine | Co-surfactant | 0.1-5 |
| Cocamide diethanolamine | Foam booster | 1-4 |
| Xantan gum or acrylate copolymer | Thickener/rheology modifier | 0-5 |
| Citric acid | pH stabilizer | 0.1-0.3 |
| Fragrance | | 0.02-0.1 |
| Water | | 49.5-89 |

Example 6

Formulation for Hair Conditioner

In this Example, a formulation for use as a hair conditioner is provided. This formulation may be used to replace or reduce polyquaternium-10, polyquaternium-7 and dimethicone oils, while preserving the easy combability and silky-soft feel that hair conditioners provide.

The formulation is shown below in Table 3.

TABLE 3

| Component | Function | Weight % |
| --- | --- | --- |
| Surfactant | Surfactant | 0.1-10 |
| Sodium cumene sulfonate | Hydrotrope | 1-3 |
| Ammonium lauryl sulfate | Surfactant | 0.1-6 |
| Ammonium laureth-3 sulfate | Surfactant | 0.1-6 |
| Cocoamide diethanolamine | Foaming agent | 0.5-2 |
| PEG-55 propylene glycol oleate | Emulsifier | 0.01-1 |
| Fragrance | | 0.02-0.1 |
| Water | | 61.9-97.2 |

Example 7

Formulation for Car Washing Detergents for Removal of Difficult Spots from the Surface In this Example, a formulation for use car washing detergents for removal of difficult spots from the surface is provided.

The formulation is shown below in Table 4.

TABLE 4

| Component | Function | Weight % |
| --- | --- | --- |
| Surfactant | Surfactant | 0.1-10 |
| Dodecyl benzene sulfonic acid or Ammonium lauryl sulfate | Foaming/ detersive agent | 5-14 |

TABLE 4-continued

| Component | Function | Weight % |
| --- | --- | --- |
| Monoethanolamine, diethanolamine, or triethanolamine | pH stabilizer | <0.5 |
| Cocoamide diethanolamine | Foam stabilizer | 0.1-2 |
| Propylene glycol | Solubilizing agent | 0.05-1.6 |
| Fragrance | | 0.02-0.1 |
| Coloring agent | | 0-0.1 |
| Water | | 71.6-95.0 |

Example 8

Formulation for a Spot-Free Rinsing or Drying Solution

In this Example, a formulation a spot-free rinsing or drying solution is provided. The solution may be applied to the windows or body of a car after the main wash is complete.

The formulation is shown below in Table 5.

TABLE 5

| Component | Function | Weight % |
| --- | --- | --- |
| Surfactant | Surfactant | 0.001-2 |
| Water | | 98-99.999 |

Example 9

Formulation for a Heavy-Duty Carpet Cleaner

In this Example, a formulation for a heavy-duty carpet cleaner is provided. The cleaner is a high-foaming deep cleaner.

The formulation is shown below in Table 6.

TABLE 6

| Component | Function | Weight % |
| --- | --- | --- |
| Surfactant | Surfactant | 1-15 |
| Dodecyl benzene sulfonic acid or Ammonium lauryl sulfate | Foaming/ detersive agent | 0.001-10 |
| Sodium cumene sulfonate | Hydrotrope | 0.001-3 |
| Monoethanolamine, diethanolamine, or triethanolamine | pH stabilizer | 0.01-1 |
| Water | | 74.95-99 |

Example 10

Formulation for a Heavy-Duty Surface Cleaner

In this Example, a formulation for a heavy-duty surface cleaner is provided. This cleaner may be used for manual or automated surface cleaning machines.

The formulation is shown below in Table 7.

TABLE 7

| Component | Function | Weight % |
|---|---|---|
| Surfactant | Surfactant | 0.001-25 |
| Dodecyl benzene sulfonic acid or Ammonium lauryl sulfate | Foaming/ detersive agent | 0.001-10 |
| Sodium cumene sulfonate | Hydrotrope | <0.5 |
| Propylene glycol | Solubilizing agent | 0.01-5 |
| Water | | 59.5-99.99 |

Example 11

Formulation for a Concentrated Graffiti Removal Detergent

In this Example, a formulation for a concentrated graffiti removal detergent is provided. The detergent may be used in a high-pressure hose.

The formulation is shown below in Table 8.

TABLE 8

| Component | Function | Weight % |
|---|---|---|
| Surfactant 4 | Surfactant | 0.001-15 |
| Sodium cumene sulfonate | Hydrotrope | 0.001-3 |
| Propylene glycol | Solubilizing agent | 0.01-5 |
| Water | | 67-99.99 |

Example 12

Formulation for a Wetting Agent in Aerosol Sprays

In this Example, a formulation for a wetting agent adjuvant in aerosol sprays is provided. The aerosol sprays may be used to apply pesticides or other crop protecting agents. The provided formulation aims to reduce the amount of surfactant chemicals in pesticide and crop protection (typically between 2-5%) by providing better performance through excellent wetting and low CMC, thus providing a greener option.

The formulation is shown below in Table 9.

TABLE 9

| Component | Function | Weight % |
|---|---|---|
| Surfactant | Co-wetting agent | 0.001-2 |
| Pesticide and/or other crop protection agent(s) | | 0.1-10 |
| Water | | 88-99.899 |

Example 13

Formulation of Additives for Aerosol Spray Paint

In this Example, a formulation for an additive for a water-based aerosol spray paint or coating is provided. The formulation aims to provide good dynamic wetting of aerosol droplets on surfaces upon application, thus preventing paint cratering and other such problems.

The formulation is shown below in Table 10.

TABLE 10

| Component | Function | Weight % |
|---|---|---|
| Surfactant | Wetting agent/ flow leveling agent/slip control agent | 0.001-5 |
| Gas propellent | Propellant | 5-30 |
| Oil-in-water emulsion | Pigmentation | 0.1-25 |
| Tamol 731A | Dispersant agent | 1-4 |
| Isopropanol (97-99% purity) | Solvent/carrier | 7-15 |
| Efka SI2022 or SI 2723 | Anti-foaming agent | 0.001-2 |
| Water | | 19-86.9 |

ASPECTS

Aspect 1 is a compound of the following formula:

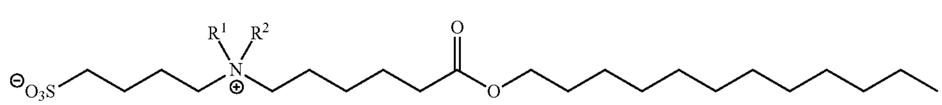

wherein $R^1$ and $R^2$ are independently chosen from $C_1$-$C_6$ alkyl.

Aspect 2 is the compound of Aspect 1, wherein the compound is 4-((6-(dodecyloxy)-6-oxohexyl)dimethylammonio)butane-1-sulfonate, having the following formula:

Aspect 3 is the compound of Aspect 1 or Aspect 2, having a critical micelle concentration (CMC) of about 0.1 mmol in water.

Aspect 4 is the compound of any of Aspects 1-3, having a plateau value of a minimum surface tension in water of about 36 mN/m.

Aspect 5 is the compound of any of Aspects 1-4, having a surface tension in water equal to or less than 37 mN/m at a concentration of 1 mmol or greater.

Aspect 6 is the compound of any of Aspects 1-5, having a surface tension in water equal to or less than 40.5 mN/m at a surface age of 4000 ms or greater.

Aspect 7 is a method of synthesizing an amino acid surfactant, comprising the steps of: (1) opening a lactam to yield an amino acid having an N-terminus; (2) reacting the N-terminus of the amino acid with an alkylating agent to yield a tertiary amine; (3) reacting the tertiary amine with an alcohol under acidic conditions to yield an amino acid ester having an N-terminus; and (4) reacting the N-terminus of the amino acid ester with a sulfonating agent to yield an amino acid surfactant of the following formula:

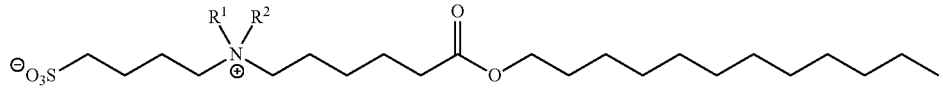

wherein $R^1$ and $R^2$ are independently chosen from $C_1$-$C_6$ alkyl.

Aspect 8 is the method of Aspect 7, wherein in step 1, the lactam is caprolactam.

Aspect 9 is the method of Aspect 7 or Aspect 8, wherein in step 2, the alkylating agent is formaldehyde or paraformaldehyde.

Aspect 10 is the method of any of Aspects 7-9, wherein in step 3, the alcohol is dodecanol.

Aspect 11 is the method of any of Aspects 7-10, wherein in step 3, the acid is p-toluene sulfonic acid.

Aspect 12 is the method of any of Aspects 7-11, wherein in step 4, the acid is hydrochloric acid.

Aspect 13 is a liquid composition comprising: a medium; and a surfactant of the following formula:

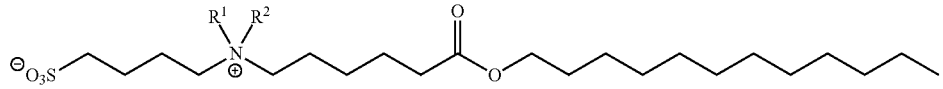

wherein $R^1$ and $R^2$ are independently chosen from $C_1$-$C_6$ alkyl.

Aspect 14 is the composition of Aspect 13, wherein the medium is water.

The invention claimed is:

1. A method of synthesizing an amino acid surfactant, comprising the steps of:
   (1) opening a lactam to yield an amino acid having an N-terminus;
   (2) reacting the N-terminus of the amino acid with an alkylating agent to yield a tertiary amine;
   (3) reacting the tertiary amine with an alcohol under acidic conditions to yield an amino acid ester having an N-terminus; and
   (4) reacting the N-terminus of the amino acid ester with a sulfonating agent to yield an amino acid surfactant of the following formula:

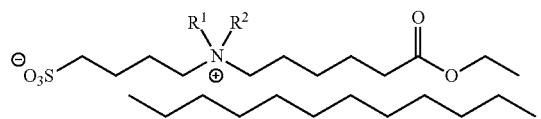

wherein $R^1$ and $R^2$ are independently chosen from $C_1$-$C_6$ alkyl.

2. The method of claim 1, wherein in step 1, the lactam is caprolactam.

3. The method of claim 1, wherein in step 2, the alkylating agent is formaldehyde or paraformaldehyde.

4. The method of claim 1, wherein in step 3, the alcohol is dodecanol.

5. The method of claim 1, wherein in step 3, the acid is p-toluene sulfonic acid.

6. The method of claim 1, wherein in step 4, the sulfonating agent is 1,4-butanesultone.

* * * * *